(12) United States Patent
Vrzalik et al.

(10) Patent No.: US 6,371,976 B1
(45) Date of Patent: *Apr. 16, 2002

(54) BODY TEMPERATURE CONTROL FOR USE WITH PATIENT SUPPORTS

(75) Inventors: John H. Vrzalik; Cesar Z. Lina, both of San Antonio, TX (US)

(73) Assignee: KCI Licensing, Inc., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,043

(22) Filed: May 22, 1998

Related U.S. Application Data

(63) Continuation-in-part of application No. 08/976,747, filed on Nov. 24, 1997, now abandoned
(60) Provisional application No. 60/031,473, filed on Nov. 25, 1996.

(51) Int. Cl.[7] .................................................. A61F 7/00
(52) U.S. Cl. ............................................ 607/104; 5/606
(58) Field of Search ............................... 602/13, 14, 27, 602/45; 607/108, 104, 96, 109, 110, 111, 114; 5/621, 606

(56) References Cited

U.S. PATENT DOCUMENTS

| | | | | |
|---|---|---|---|---|
| 2,804,911 A | * | 9/1957 | Howarth | 155/182 |
| 2,930,594 A | * | 3/1960 | MacCracken | 257/306 |
| 3,867,939 A | * | 2/1975 | Moore et al. | 128/254 |
| 4,114,620 A | * | 9/1978 | Moore et al. | 128/254 |
| 4,677,970 A | * | 7/1987 | Green et al. | 128/82.1 |
| 4,867,230 A | * | 9/1989 | Voss | 165/46 |
| 5,411,541 A | * | 5/1995 | Bell et al. | 607/104 |
| 5,486,207 A | * | 1/1996 | Mahawili | 607/104 |
| 5,640,728 A | * | 6/1997 | Graebe | 5/606 |

* cited by examiner

*Primary Examiner*—Linda C. M. Dvorak
*Assistant Examiner*—Jocelyn Ram

(57) ABSTRACT

A thermally controllable apparatus for use with a predetermined therapeutic support platform apparatus and a thermia fluid producing device, wherein said apparatus includes a first side configuratively disposed adjacent the patient surface of the support platform, a second side disposed adjacent a patient and having a first portion thereof sealably connected to a first portion the first side and a second portion thereof spaced from a second portion of the first side such that there is formed a pocket therebetween and valve means operably connected to the pocket and to the thermal fluid producing device to permit fluid flow therebetween and a method of using the same.

10 Claims, 13 Drawing Sheets

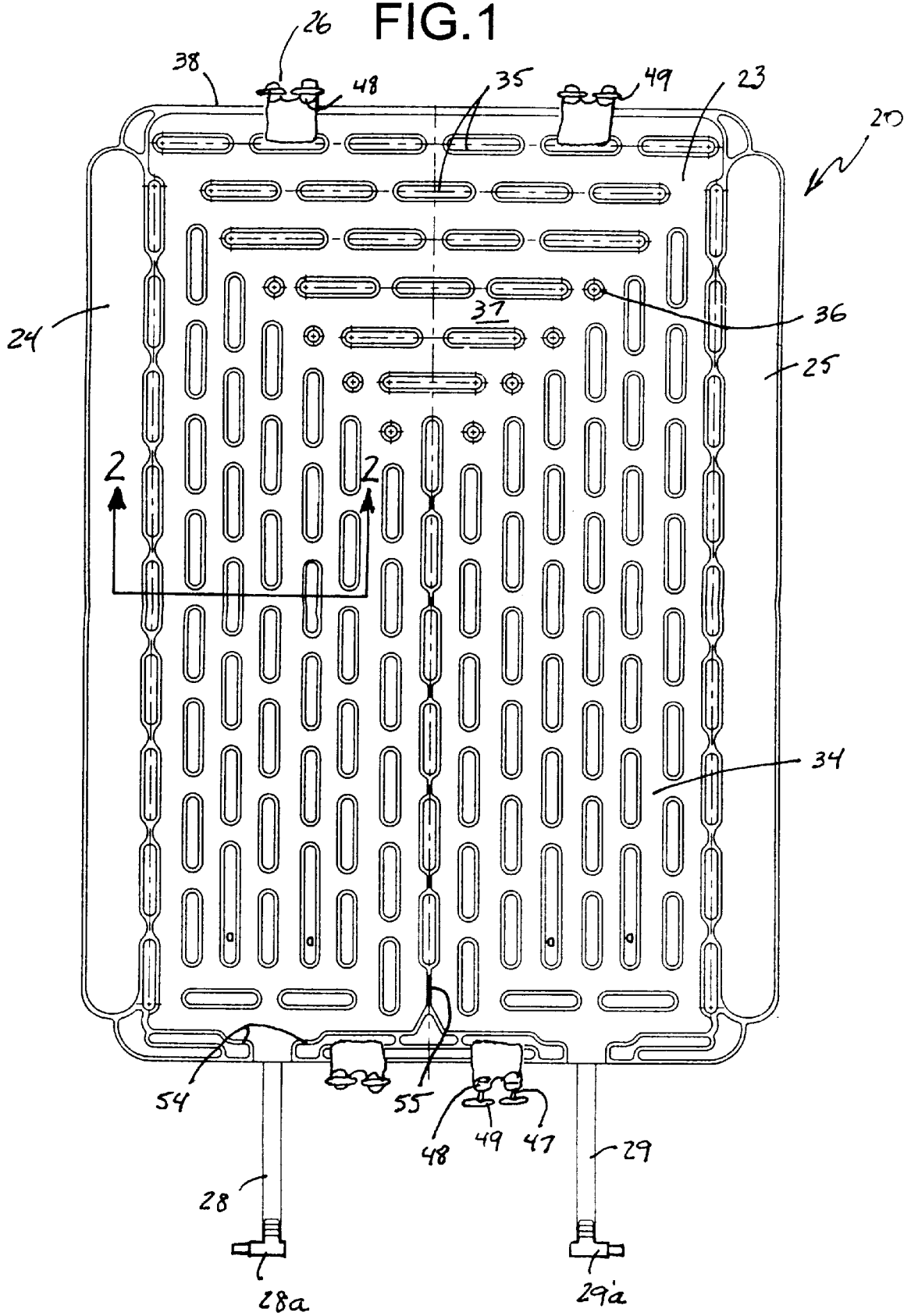

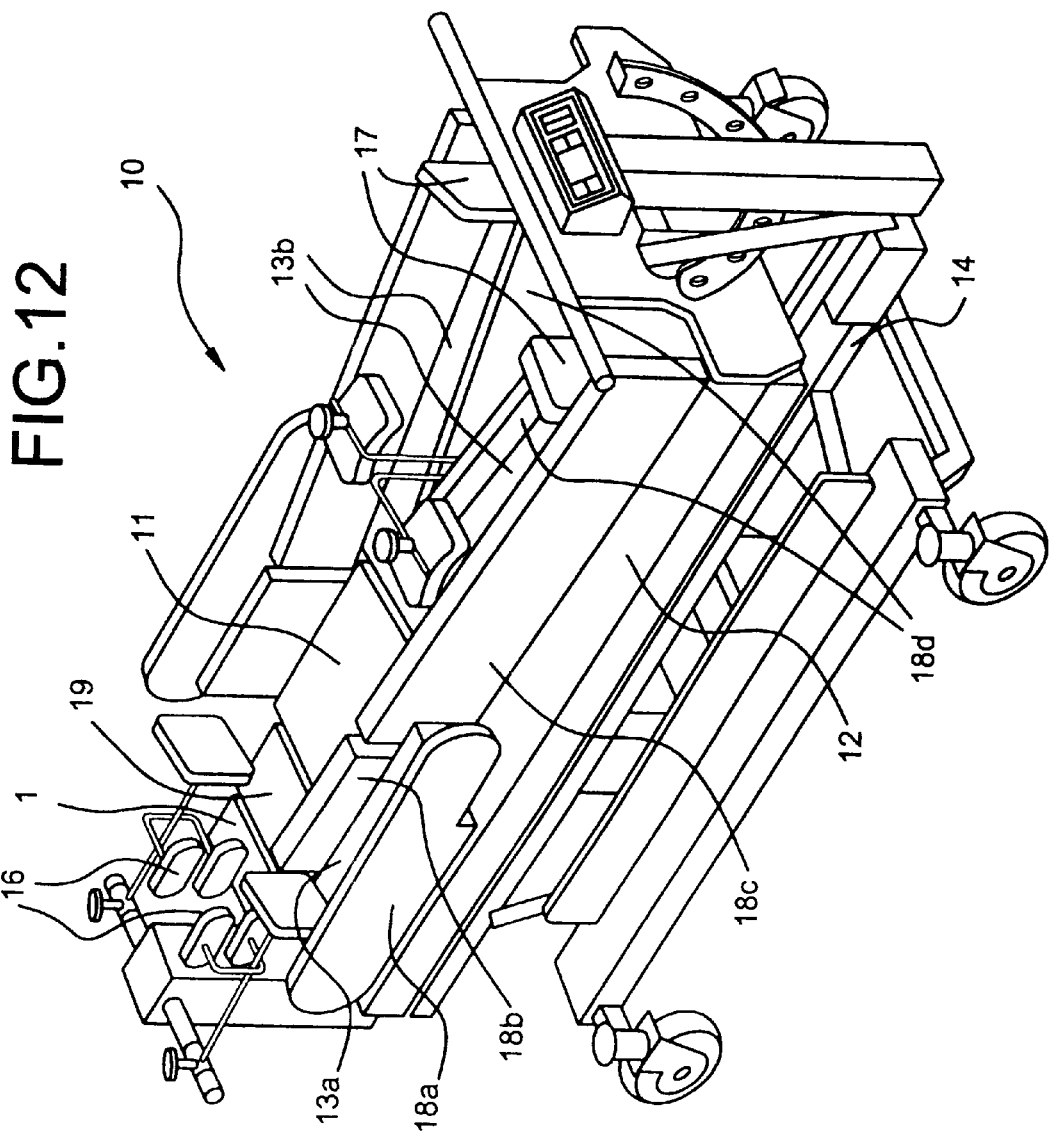

BODY TEMPERATURE CONTROL FOR USE WITH PATIENT SUPPORTS

This application is a continuation-in-part of Applicant's co-pending U.S. application Ser. No. 08/976,747, filed Nov. 24, 1997. Ser. No. 08/976,747 was a continuation of provisional application No. 60/031,473 filed Nov. 25, 1996. Applicant hereby claims the benefit of the earlier filing dates of these prior applications under 35 U.S.C. 119(e)(1) and 120.

BACKGROUND OF THE INVENTION

The present inventions relate to apparatus and methods for affecting a patient's body temperature, particularly for therapeutic applications. There are broader applications, such as with heating pads and the like and in any application in which there is a need to reduce or prevent heat/moisture build-up between a person's body and a support surface with which the patient's body is in contact, but the present inventions relate primarily to cooling pads and systems for lowering a patient's body temperature. Intended fields include applications for patients with diminished health and for patients using therapeutic supports such as oscillating treatment platforms, pressure reducing mattresses, and low air loss beds, to name a few.

Various types of devices have long existed for cooling and heating patients without much regard for accommodating other health care needs. Such devices typically use a heat exchanger in a form of a flexible pad that can be positioned close to the patient's skin. Because of the way such pads work, they have traditionally been fluid impervious, which can trap moisture (i.e., condensation, sweat, incontinence, etc.) in close proximity to a patient's skin.

High moisture levels, however, tend to promote maceration and skin-breakdown. To make matters worse, the lower temperatures induced by cooling pads might naturally constrict a patient's capillaries, which may reduce the flow of oxygen and nutrients to the skin. Such effects would be of particular concern in patients who have poor skin condition or compromised circulation from the start. Hence, conventional cooling pads may create an environment that is less than ideal for skin care.

For many of the same patient populations, there have also long been many types of specialized patient supports adapted to facilitate skin care. Two notable types of specialized therapeutic supports are (i) pressure reducing mattresses for reducing the pressures exerted by a mattress against a patient's skin (referred to as "interface pressures"), and (ii) oscillating treatment platforms for rotating patients from side-to-side. (For present purposes, low air loss mattresses and other pressure relieving mattresses are grouped together with pressure reducing mattresses.) Commercial examples of pressure reducing mattresses are available through KCI Therapeutic Services, Inc. of San Antonio, Tex., under the THERAREST™ (for composite foam mattresses) and FIRST STEP™ (for low air loss mattresses) trademarks. Detailed descriptions of particular pressure reducing mattresses may be found in U.S. Pat. No. 5,022,110 issued Jun. 11, 1991 (Stroh) and U.S. Pat. No. 3,644,950 issued Feb. 29, 1972 (Lindsay).

Oscillating treatment platforms are useful in treating and/or preventing a wide range of illnesses and conditions. Such a platform is particularly useful in addressing complications that may be encountered with immobile patients, including bed sores and other skin problems. By automatically rotating the patient from one lateral side to the other on a periodic basis, interface pressures at any particular location are likewise varied. As always, though, excess moisture near the patient's skin site tends to increase the likelihood of further skin problems. Commercial examples of oscillating treatment platforms are available through KCI Therapeutic Services, Inc. of San Antonio, Tex., under the ROTO REST™ trademark. Particular examples are also described in U.S. Pat. No. 3,343,165 issued on Mar. 25, 1969 (Keane) and U.S. Pat. No. 4,175,550 issued on Nov. 27, 1979 (Leininger et al.).

The descriptions (including drawings) of each of the above patents and all other patents referenced elsewhere in this application are incorporated herein by this reference, as though set forth in their entirety.

Despite the importance and high costs of skin care, the need to use hyper and/or hypothermia pads often overrides any concerns about the moist skin climate often associated with use of such pads. As a consequence, the therapeutic benefits of a patient's specialized support may be diminished. Consider low air loss ("LAL") mattresses, for instance. Perhaps the most important benefit of a LAL mattress is the slow but continuous evacuation of moisture vapor from adjacent the skin. Typical LAL mattresses support the patient with air cushions made from vapor-permeable fabrics. The vapor permeable material allows moisture vapor near the skin to pass away from the skin, and a continuous flow of air keeps the cushions inflated while also evacuating the moisture vapor that has passed through the fabric. Such benefits are significantly impeded by introducing a cooling pad which is impervious to fluid between the patient and the air cushions of the LAL mattress.

As can be seen, although numerous specialized patient supports are generally useful in minimizing skin breakdown and in otherwise treating or preventing various ailments, there remains a need to improve such products and the conditions under which they may be used. There is also a therapeutic as well as a comfort need to improve thermal pads and the environments in which they are used.

SUMMARY OF THE INVENTIONS

It is a basic object of the present inventions to promote patient health by improving available therapies. This object may be addressed in part by improving devices for patient temperature control, such as by improving the functionality, efficiency, ease-of-use, comfort, safety and effectiveness of such devices.

It is another basic object to improve patient supports, particularly by enabling patient temperature control as an adjunct to other benefits of patient supports. It is a related object to enable patient temperature control using cooling pads and the like without compromising patient skin condition or impeding other therapies, including low air loss therapy and continuous lateral rotation therapy.

Accordingly, the present invention is directed in part to patient temperature control on a patient support. Such control may include use of a thermally controlled sheet (such as a pad or blanket) through which a heat transfer fluid is circulated. The sheet typically defines two types of passages—an enclosed array of fluid passages for directing the heat transfer fluid, and cross passages or the equivalent for passage of other fluids from one face of the sheet to the other. As gas passages, the cross passages permit air and/or moisture vapor to pass from one side of the sheet to the other, thereby addressing many objects including the object of enabling the provision of thermal control as an adjunct to low air loss therapy. As an open hole or the like through the thermal sheet, the cross passages may also permit liquids such as condensation, sweat, body fluids, etc. to pass away from a patient's skin, thereby minimizing maceration and skin breakdown.

Embodied as an under-patient pad, one face of the sheet faces the patient while the opposite sheet faces the patient support. The sheet is typically formed by welding the two faces together in a way that forms a plurality of pocket passages therebetween. Liquid and/or vapor cross-passages or other types of openings are formed between the pocket passages. Lines are provided to operably connect the pocket passages with a conventional hyper-hypothermia unit to permit fluid flow therethrough and the sheet is welded at intervals forming the fluid passages which are spaced and arranged so as to direct the flow of fluid therethrough throughout the entire sheet. Hook and pile tabs and/or other fasteners are provided at opposite ends of the pad for anchoring or for combining the pad with other similar pads to affect a larger surface area and on the side edges of the pads for securing the pad to a patient support surface.

The thermal control sheet may be configured to wrap around at least a part of the patient in certain applications. Alternating flows may also be used. The invention also includes various therapeutic methods for facilitating patient care.

Many objects and advantages will be readily apparent to those skilled in the art upon viewing the drawings and reading the detailed description hereafter, particularly when considered in light of the appended claims and the related art.

BRIEF DESCRIPTION OF THE DRAWINGS

FIG. 1 is a plan view of a cooling pad which represents one preferred embodiment of various aspects of the present invention.

FIG. 12 is a headward perspective of an oscillatory therapeutic support platform.

DETAILED DESCRIPTION OF THE PREFERRED EMBODIMENTS

Various preferred embodiments of a thermally controlled sheet, or pad, in the form of various cooling pads, thermal sheets, and body wraps, constructed in accordance with the teachings of the present invention are described below. These embodiments collectively represent notable innovations for cooling patients in conjunction with various patient supports such as mattresses, beds, seat cushions and the like. For the most part, these descriptions first describe structure and manufacture of the embodiments and then describe their typical use and some of the benefits of their structure in connection with such use.

Figure 1A:
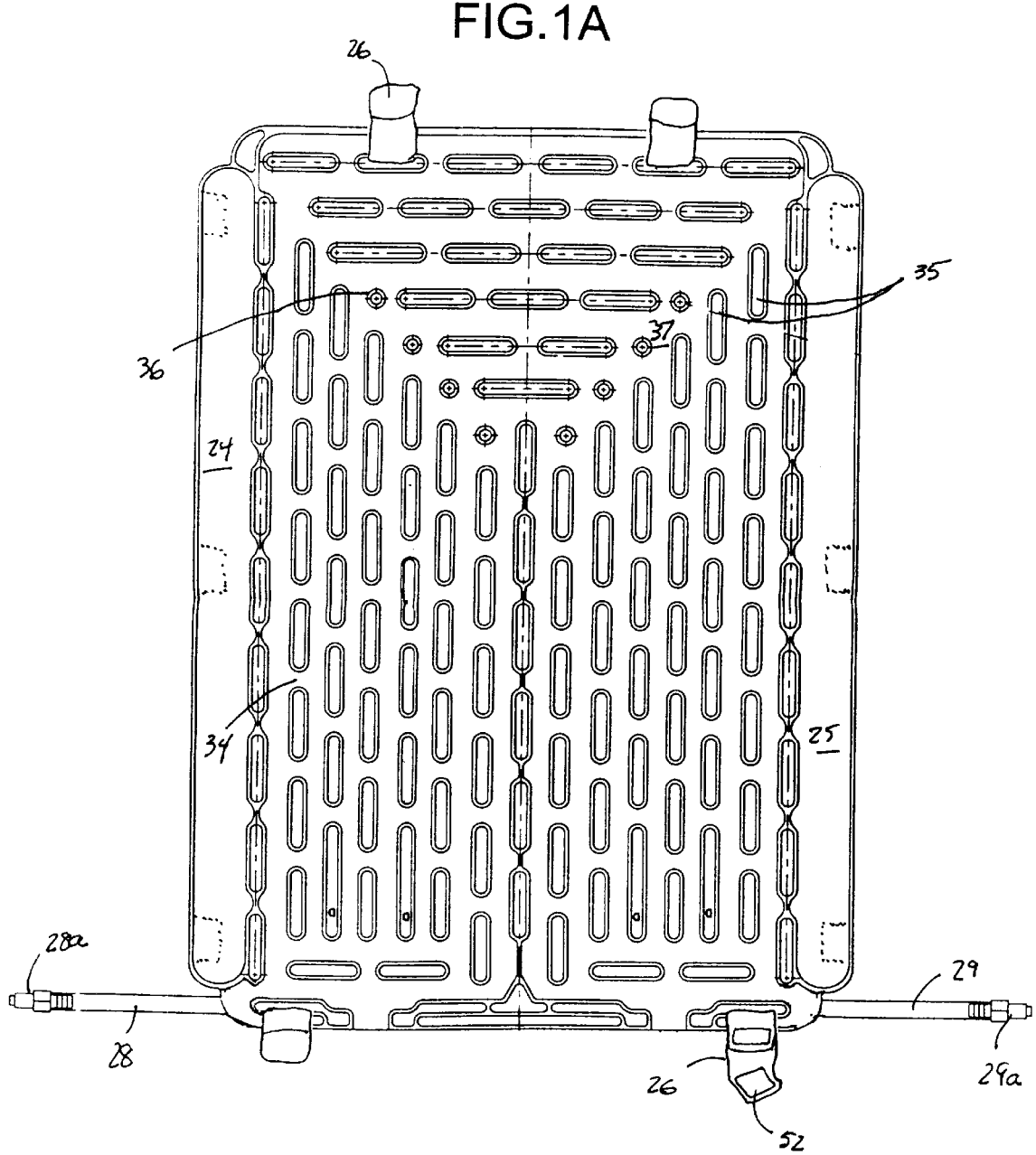
FIG. 1A is a plan view of a second preferred embodiment of the cooling pad of FIG. 1.
Figure 2:
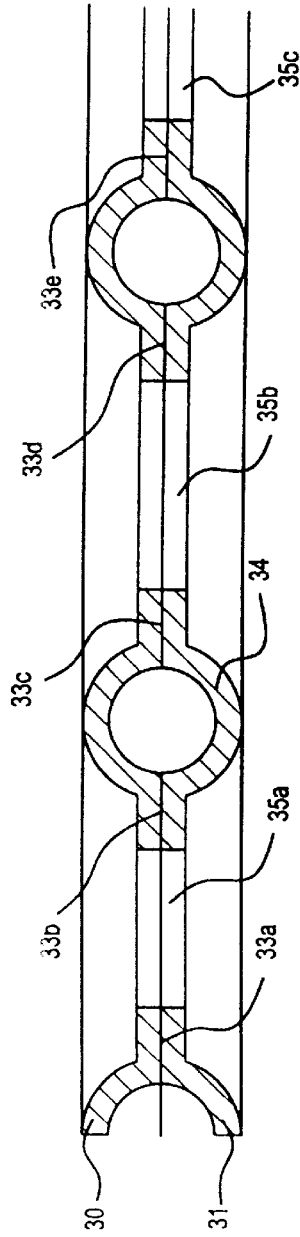
FIG. 2 is a partial cross-sectional view of the cooling pad shown in FIG. 1 taken along the lines 2—2 in FIG. 1.

Referring to the drawings, FIGS. 1, 1A, and 2 show detailed aspects of a thermally controlled sheet in the form of a cooling pad 20 that represents a preferred embodiment of various aspects of the present invention. Pad 20 generally comprises heat exchanger 23, integral tabs 24 and 25, and fluid lines 28 and 29.

As viewed in FIG. 1, heat exchanger 23 is generally rectangular in shape. The longer dimension of heat exchanger 23 is approximately thirty inches, which is slightly less than the width dimension of most standard hospital bed mattresses. The shorter dimension of heat exchanger 23 is approximately 20 inches. Although shown in FIGS. 1 and 1A extending along almost the entire length of the edges of the long dimension of heat exchanger 23, those skilled in the art who have the benefit of this disclosure will recognize that the tabs 24 and 25 need not extend along that entire edge and/or that the tabs 24 and 25 may be comprised of a plurality of tabs of much shorter dimension spaced along the length of the edges of the long dimension of heat exchanger 23.

Heat exchanger 23 and its integral tabs 24 and 25 are comprised primarily of a flexible, RF-weldable material suitable for containing and directing the flow of a heat transfer fluid for use in for controlling the body temperature of patients. In a particularly preferred embodiment, water, at temperatures and pressures such as are generated by conventional hyper-hypothermia units, is the heat transfer fluid which is circulated through heat exchanger 23. The embodiment of FIG. 1 is preferably comprised of ten-mil PVC sheets 30 and 31 (FIG. 2). Absent modifications described further herein, the two sheets 30, 31 are substantially identical to each other and are RF-welded together and cut in a manner that provides a relatively flat array 37 of fluid passages 34 bound by welds 33. Cooling pad 20 is also formed with a perimeter weld 38 surrounding the perimeter of the array 37, which seals the perimeter of sheets 30 and 31 together. In one alternative embodiment (not shown), one or both of the outer surfaces of sheets 30 and 31 is provided with a flocked finish. In another embodiment (also not shown), the entire heat exchanger 23 of pad 20 is enclosed in and/or integral with a fabric cover which is permeable to air.

The array 37 preferably has a shape and configuration substantially as shown in FIG. 1, which is adapted to promote circulation of the heat transfer fluid throughout each of the fluid passages 34. The array 37 of fluid passages 34 defines a corresponding array of oblong holes 35 and circular holes 36, or cross passages between the fluid passages 34. When passages 34 are filled with heat transfer fluid, welds 33 and cross passages 35, 36 give the effect of an array of dimples arranged between the passages 34 that ensure substantially uniform thickness of the pad 20. As can be seen in FIG. 1, pad 20 is provided with 123 oblong dimples 35 and eight circular dimples 36, although various configurations and assortments of dimples (or holes) 35, 36 can be utilized to advantage. The particular pattern of dimples shown tends to orient the longitudinal dimension of oblong dimples 35 parallel with the closest outer edge of array 37. Such orientation is thought to promote better circulation of heat transfer fluid from inlet port 28b throughout the entirety of array 37 before exiting the array outlet port 29b. In the particularly preferred embodiment, various flow-directing welds 54, 55 are utilized to promote circulation of the heat transfer fluid throughout the entire array 37. Formation of such flow-directing welds, including auxiliary division welds (not shown), may require some experimentation to obtain proper radiuses and locations through optimized strength and durability of the pad as a whole, as will be known to those of skill in the art.

Also provided along the edges of the shorter dimension of pad 20 are one or more fasteners 26 for securing the pad 20 to the support surface 12 (see FIG. 12) of a patient therapeutic support 10. In the embodiment shown, fasteners 26 take the form of an elastic strip 47 affixed to flaps 48 formed of a piece of fabric having a hole therein for receiving a button 49 for looping the strap around a portion of the support surface 12 to secure the pad 20 to the support surface.

Figure 3:
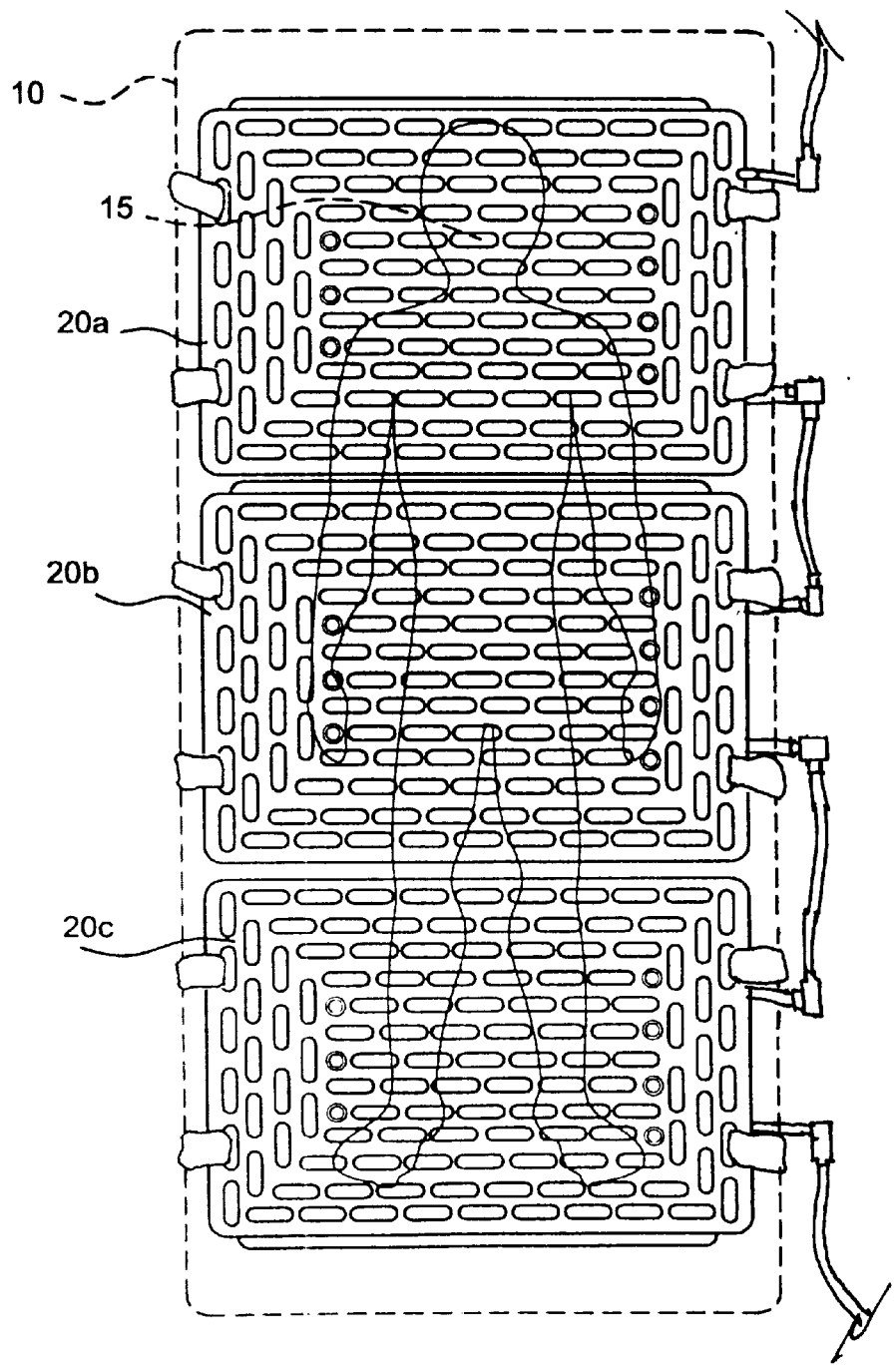
FIG. 3 is a plan view of one embodiment of the cooling pad of the present invention as operatively implemented together with two other identical pads for cooling a patient (shown in phantom line) supported on a mattress (shown schematically in dashed line).

An alternative embodiment of the cooling pad of the present invention is illustrated in FIG 1A. This second preferred embodiment varies from the embodiment shown in FIG. 1 in the type of fasteners 26 and in the configuration of the liquid line quick disconnect fittings 28a, 28c, 29a and 29c. Instead of buttons and elastic strips, the fasteners 26 of the pad shown in FIG. 1A are comprised of a strip 52 of hook and pile fasteners for looping around a portion of the support surface 12 of a therapeutic patient support (not shown) or adhering directly to a complementary strip of hook and pile fasteners on the support surface 12. Regarding the configuration of the fittings, as shown in FIG. 1, the fittings 28a and 29a of fluid line 28 and fluid line 29, respectively, are right angle fittings which swivel 360° on the end of lines 28 and 29 to facilitate coupling a plurality of the cooling pads 20 in end-to-end fashion as shown in FIG. 3. Because the lines 28 and 29 of the cooling pad 20 shown in FIG. 1A are connected to the pad along the edge of longer dimension, or at least close enough to the corner of the pad 20 as to be directed outwardly from the pad in a direction which is substantially perpendicular to the edge along the longer dimension of pad 20, the fittings 28a and 29a are straight fittings and do not need to be swiveling right angle fittings.

Although the connectors 28a and 29a shown in FIGS. 1 and 1A are both male in gender for convenient connection to conventional hyper-hypothermia units, in an alternative embodiment (not shown) one or the other of the fittings 28a or 29a is male in gender and the other fitting is female. With this embodiment, the heat exchanger pads can conveniently be connected together without the use of gender changing adapters. Those of skill in the art will readily recognize that the embodiment illustrated in FIG. 1 can also be connected to another like heat exchanger through the utilization of male-to-male gender adapters.

The tooling for RF-welding exchanger 23 is preferably of the conventional tear-and-seal type. As such, the tooling both forms the welds 33 and cuts the holes 35, 36 in a single operation, thereby minimizing the need for indexing and registry of the material between stamping and cutting operations. Because of the symmetrical nature of array 37, exchanger 23 can be formed using a two-stage process of stamping one lateral side of array 37, flipping the array 37 over, and then stamping the opposite lateral side of array 37. Such a two-stage forming process may help reduce tooling costs.

Tabs 24 and 25 are also formed at each lateral edge of pad 20 and are equipped with hook-and-pile strips 41–46 (shown in shadow lines in FIG. 1A) to enable connection to adjacent pads, such as shown in FIG. 3. Hook and pile connector strips are mounted on the opposing tabs 24 and 25, three on each side, with pressure sensitive adhesive. Hence, three or four pads are connected in series to provide a full-length patient cooling pad for providing a heat transfer thermal layer beneath the full-length of a patient laying a therapeutic support. Although separate hyper-hypothermia units could be provided for each pad in such a series, the same series may be served by a single unit by connection of the liquid lines in the manner shown in FIG. 3.

Fluid lines 28 and 29 are conventional liquid lines suitable for conveying cooling liquids pumped by a conventional hyper-hypothermia unit (not shown). Conventional ¼-inch I.D. by ⅜-inch O.D. clear 70F non-toxic PVC tubing, such as is available under the "Kuri Tec K010" designation from Accuflex, Canada, is suitable for lines 28 and 29. The distal ends of fluid lines 28 and 29 are adapted with quick-disconnect fittings 28a and 29a, respectively, for operative connection to the outlet and inlet of a hyper-hypothermia unit (not shown). Male CPC fittings are suitable for fittings 28a and 29a. Fittings 28a and 29a are preferably of the type that have integral check valves that close when the fittings 28a, 29a are not operatively engaged within a corresponding female connector. Such check valves serve to minimize leaks of heat transfer fluid upon disconnecting lines 28 and 29 from the hyper-hypothermia unit. Line 28 is intended for connection to the outlet of the hyper-hypothermia unit for receiving a flow of heat transfer fluid from the hyper-hypothermia unit. Line 29 is intended for connection to the return inlet of the hyper-hypothermia unit for returning the flow of heat transfer fluid to the hyper-hypothermia unit. In the preferred embodiment, however, fittings 28a and 29a are identical and their connections to the hyper-hypothermia unit may therefore be reversed. In alternate embodiments, one of the two fittings 28a, 29a is replaced with a male or female fitting, as the case may be, or distinguished in some other fashion as known in the art, to ensure consistent connection of lines 28 and 29 to the respective outlet and inlet of the hyper-hypothermia unit. Appropriate adaptation of the lines from the hyper-hypothermia unit may be required to accommodate sealed connection with the particular fittings 28a and 29a.

The proximal ends 28b and 29b of fluid lines 28 and 29 are integrally bonded to the perimeter of heat exchanger 23, in a manner which communicates heat transfer fluid from lines 28 and 29 into the array of fluid passages therein. The integral connection is preferably achieved by inserting the proximal ends of lines 28 and 29 between the two opposing sheets of exchanger 23. Once so inserted, the proximal ends are welded in place by a separate R-F welding operation, welding the proximal ends between opposing sheets of exchanger 23. Such welding seals the lines into sealed communication with the enclosed array of exchanger 23.

Although the lines 28 and 29 are shown welded into the exchanger 23 of cooling pad 20 along the edge of the shorter dimension, it will be understood by those skilled in the art who have the benefit of this disclosure that the lines 28 and 29 can also be welded into the exchanger 23 along the edge of longer dimension. Welding the lines 28 and 29 into the exchanger along the edge of the longer dimension has the advantage of simplifying the connection of a plurality of pads 20a, 20b, and 20c as shown in FIG. 3. To further facilitate the connection of a plurality of pads in series with each other, the fittings of such pads are preferably male and female on each pad so as to require sequential assembly of the pads. Also in this alternative embodiment, the shape of the lines 28 and 29 at the point at which they are welded into exchanger 23 may cause a bulge in the exchanger which could compromise the comfort and/or care of the patient. To prevent and/or reduce the size of this bulge, the lines 28 and 29 may be flat lines and/or the orifice into which the lines are welded is of larger diameter than the diameter of the lines 28 and 29.

In FIG. 1A, the lines 28 and 29 are, in turn, connected to the outlet and inlet of a hyper-hypothermia unit (not shown). Female CPC fittings are suitable for fittings 28a and 29a. Fittings 28a and 29a are preferably of the type that is provided with an integral check valve that closes when the fittings 28a, 29a are not operatively engaged within a corresponding male connector to minimize leaks of heat transfer fluid upon disconnecting lines 28 and 29 from the hyper-hypothermia unit. Line 28 is intended for connection to the outlet of the hyper-hypothermia unit for receiving a flow of heat transfer fluid from the hyper-hypothermia unit. Line 29 is intended for connection to the return inlet of the hyper-hypothermia unit for returning the flow of heat transfer fluid to the hyper-hypothermia unit. In the preferred embodiment, however, fittings 28a and 29a are identical and their connections to the hyper-hypothermia unit may therefore be reversed. In alternate embodiments, one of the two fittings 28a, 29a may be replaced with a male and/or female connector as the case may be, or otherwise distinguished from the other connector in a manner known in the art, to ensure consistent connection of lines 28 and 29 to the respective outlet and inlet of the hyper-hypothermia unit. Appropriate adaptation of the lines from the hyper-hypothermia unit may be required to accommodate sealed connection with the particular fittings 28a and 29a.

Figure 13:
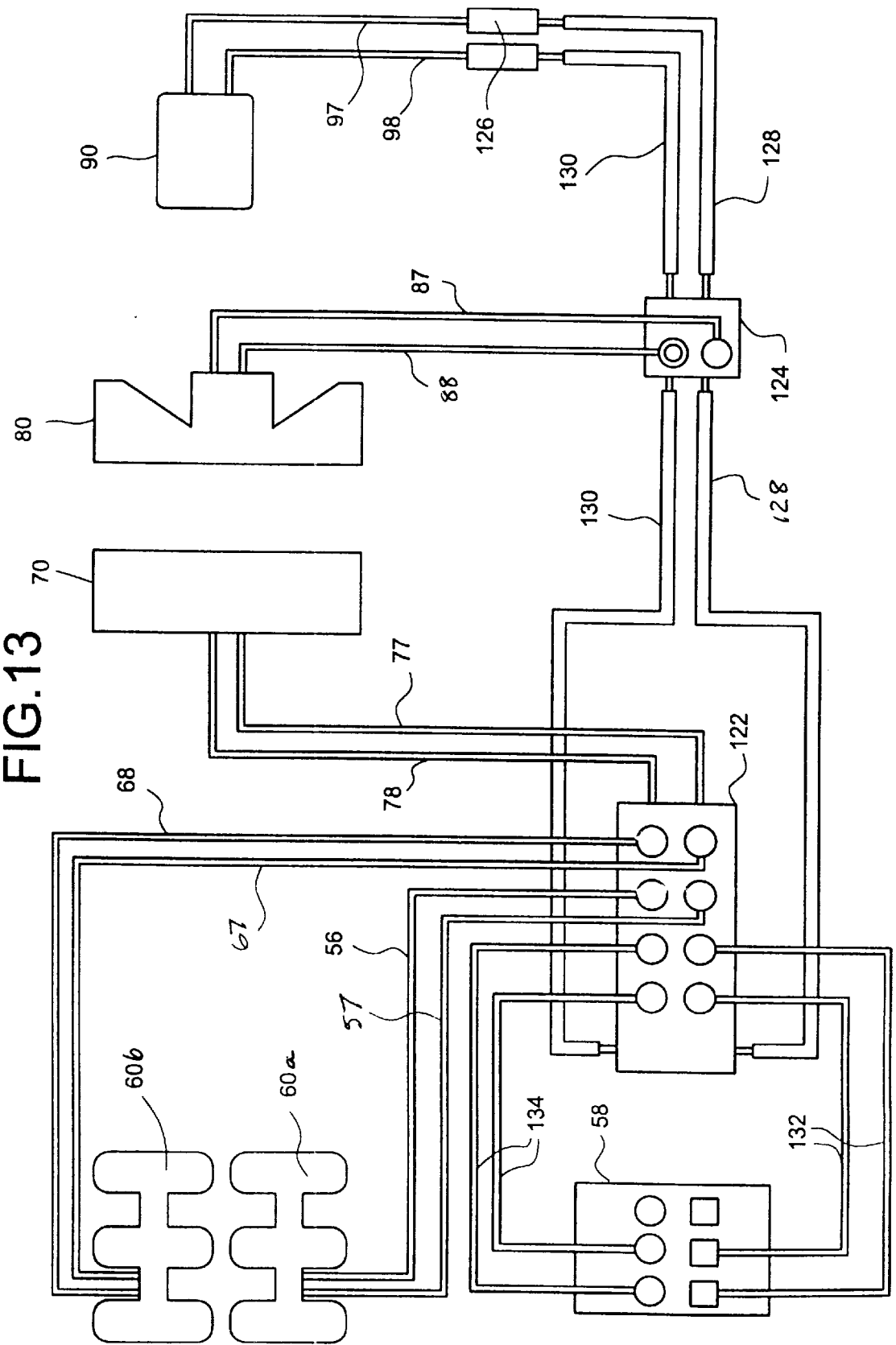
FIG. 13 illustrates a schematic diagram of a control system for a plurality of thermally controlled body wraps constructed in accordance with the present invention and utilizing a hyper-hypothermia fluid producing and distribution device.

A preferred embodiment of a complete system for controlling the body temperature of a patient in accordance with the present invention includes at least one cooling pad 20 operatively connected to a conventional hyper-hypothermia unit as shown at reference numeral 58 in FIG. 13. The "Blanketrol II," Model 222R unit (available from Cincinnati Sub-Zero Products, Inc., Cincinnati, Ohio) is an example of a conventional hyper-hypothermia unit with which pad 20 may be used in a preferred cooling system. Non-specific references herein to a "standard" or "conventional" hyper-hypothermia unit or cooling unit should be understood to include units of this type. Fluid lines 128 and 130 are conventional fluid lines suitable for conveying heat transfer fluids pumped by a conventional hyper-hypothermia unit.

Referring to FIG. 3, as with other thermal layers, the primary function of cooling pad 20 is the enable circulation of thermal heat transfer fluids over an area in proximity to a patient to permit heat transfer between the patient and the fluid. Cooling pad 20 is considered to be "transmissive" in that air and water vapor are allowed to pass through one phase separate cooling pad 20 to the other phase thereof. The transmissive feature of cooling pad 20 resulting from the presence of cross passages 35, 36 enables the use of the pad 20 of the present invention between the lower surface of a patient 15 and the upper surface of a therapeutic support 10 while allowing a low air loss surface to pass air into the space in proximity to the lower surface of the patient, thereby allowing moist vapor to be evacuated from the environment next to the patient's skin to enhance the microclimate for optimal patient skin condition.

Accordingly, FIG. 3 is a plan view of a cooling pad 20a, such as the cooling pad 20 shown in FIG. 1 or FIG. 1A, as operatively implemented together with pads 20b and 20c for cooling a patient 15 (shown in phantom line) supported on therapeutic support 10 (shown in dashed line). Although shown in FIG. 3 as being identical, those skilled in the art will recognize from this disclosure that the pads 20a, 20b and 20c may each vary in their configuration and/or be identical to each other. Regardless of their configuration, pads 20a, 20b, and 20c are positioned adjacent each other and, if the pads are provided with the releasable hook and pile tabs 41–46, each pad is connected to its adjacent pad to ensure their positioning. Alternatively, the pads are secured to the support surface 12 of therapeutic patient support 10 by the fasteners 26.

As illustrated in FIG. 2, other aspects of the present invention are appreciated by modifying or replacing the composition of sheets 30 and 31 or by otherwise combining different materials with pad 20. Particularly, in one alternative embodiment, an absorptive pad (not shown) is secured to the outer surface 30a of the lower sheet 30 of heat exchanger 23. Vapor-permeable absorptive pads, such as are commercially available under the trademark DRIFLO™ from KCI Therapeutic Services, Inc. of San Antonio, Tex., are preferred. Although adhesives or the like may be used for more secure mounting of such an absorptive pad on surface 30a, Applicant has found that the hook-matrix strips 44–46 of tab 25 tend to releasably engage the fabric of said preferred absorptive pads. Hence, to secure such an absorptive pad to pad 20, the absorptive pad is laid flat in the center of mattress 10 and pad 20 is then positioned on top of the absorptive pad, in approximately the same general region as the absorptive pad, but in a position such that tab 25 overlaps an edge of the absorptive pad. When patient 15 is then positioned on pad 20 (or when strips 44–46 are otherwise pressed against the absorptive pad), the absorptive pad is releasably secured to the outer surface 30a of pad 20 by strips 44–46. Such releasable securement services to ensure optimal positioning directly beneath pad 20. Thence, the absorptive pad can not only be used to absorb incontinence and other body fluids, but it is also ideally positioned to absorb even the minimal condensation that is not evaporated by the passage of air through cross passages 35, 36 which may collect on pad 20. Due to the releasable securement, the absorptive pad can then be removed, discarded and replaced as a disposable separate from pad 20, which is likely to be reusable.

Rather than (or in addition to) the above-described combination of a DRIFLO™ pad together with pad 20, similar purposes are addressed in another alternative embodiment by bonding an absorptive layer (not shown) on the outer surface 30a of the lower sheet 30 of heat exchanger 23, FIG. 2. Using a thin sheet of PVC foam material as the absorptive layer, such a construction is perhaps best achieved by using an adhesive to bond the absorptive layer to surface 30a before the RF welding process (described elsewhere herein) such that the absorptive layer is welded and cut in place at the same time as sheets 30 and 31. In use, pad 20 is then positioned on mattress 10 with the absorptive layer facing away from the patient 15 to draw moisture away from patient 15. With this configuration (as well as with the DRIFLO™ combination described previously), the absorptive layer is able to also serve the additional purpose of insulating pad 20 from heat that might be conducted or radiated from mattress 10. For that matter, such an absorptive layer also helps insulate pad 20 from heat that might be conducted or radiated from anywhere else outside surface 30a, such as from a lamp above the patient if pad 20 is placed on top of patient 15 or is wrapped around part of the patient 15.

Other aspects of the present invention are appreciated by bonding an insulative layer (not shown) on the outer surface 30a of the lower sheet 30 of heat exchanger 23. Using a thin sheet of PVC foam material as the insulative layer, such a construction is perhaps best achieved by using an adhesive to bond the insulative layer to surface 30a before the RF welding process (described further herein) such that the insulative layer is welded and cut in place at the same time as sheets 30 and 31. In use, pad 20 is then positioned on mattress 10. For that matter, such an insulative layer would also help insulate pad 20 from heat that might be conducted or radiated from anywhere else outside surface 30a, such as from a lamp above the patient if pad 20 is placed on top of patient 15 or is wrapped around part of the patient 15.

Figure 4:
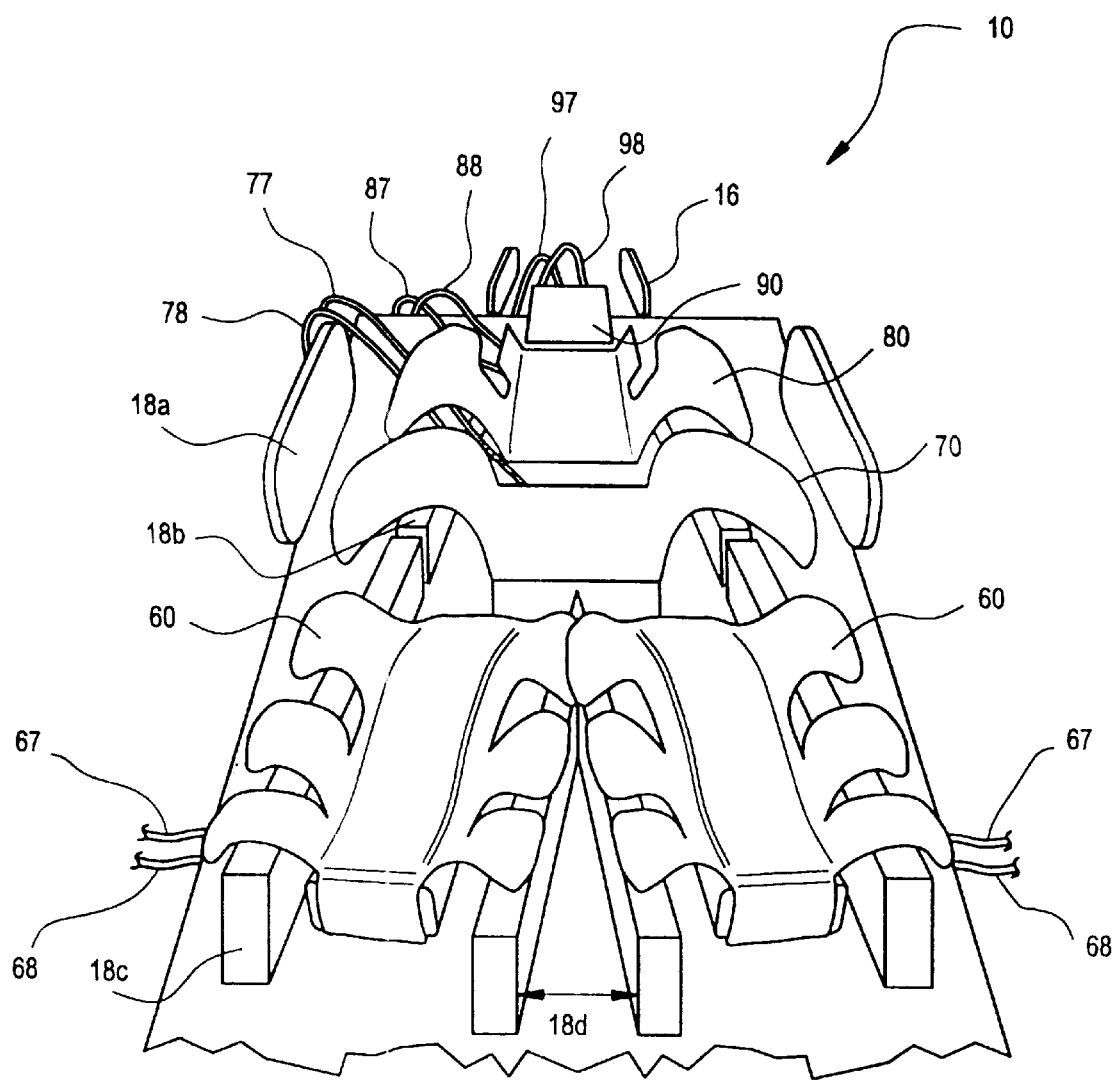
FIG. 4 is a partial, headward perspective view of an oscillatory patient support platform having four cooling pads operatively positioned thereon, representing alternate embodiments of various aspects of the present invention.
Figure 11:
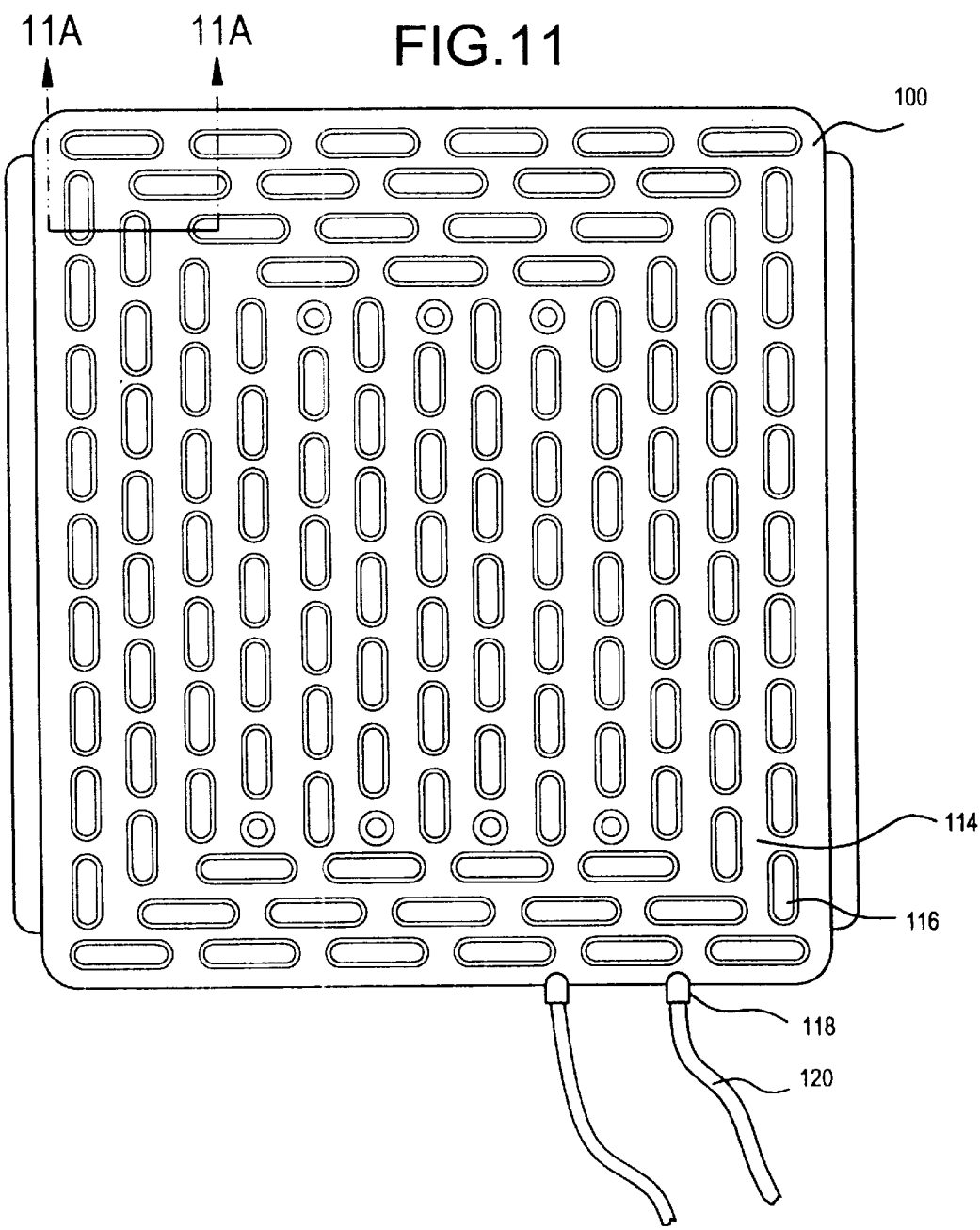
FIG. 11 illustrates another embodiment of the thermally controlled body wrap of the present invention which employs multiple layers of liquid passages and provides for air exchange through the wrap.

FIG. 4 is a partial, headward perspective view of an oscillatory patient support platform 10 having cooling pads 60, 70, 80 and 90, representing alternate embodiments of thermally controlled sheets or pads constructed in accordance with the teachings of the present invention, operatively positioned thereon. There is shown in FIG. 4 the top surface of a therapeutic support platform apparatus 10 of the general type shown in U.S. Pat. No. 3,343,165 issued to F. X. Keene on Mar. 25, 1969, U.S. Pat. No. 4,175,550 issued to James R. Leininger et al. on Nov. 27, 1979, and U.S. Pat. No. 4,730,606 issued to Peter A. Leininger on Mar. 15, 1988 as depicted in FIG. 11. Each of such U.S. patents are incorporated hereinto for any and all purposes by this specific reference. Preferably, support platform 10 is a device commercially available under the trademark ROTO REST DELTA™ from KCI Therapeutic Services, Inc. of San Antonio, Tex. Although the therapeutic support platform 10 illustrated is of the type shown, those skilled in the art who have the benefit of this disclosure will recognize that the support platform 10 could be any support platform in which there is a need to control heat/moisture build-up at the interface between the surface of the support platform and the skin of the patient supported thereon. Such a surface could be the seat of a wheelchair, a so-called "bead" bed, or any of the support platforms described herein.

However, the thermally controlled heat transfer sheet of the present invention is particularly well adapted for use in connection with a patient support surface of the type illustrated in FIG. 12. Such therapeutic support platforms 10 include a support surface 12 operably connected to a support frame 14 in a manner to permit oscillation of the support surface 12 relative to the support frame 14. The therapeutic support platform 10 has head retention members 16, side retention members 18a, 18b, 18c and 18d and feet retention members 17, all of which are positionably connected to the support surface 12 and also shown in FIG. 4 and which function to confine the patient on the support surface 12. The fasteners 26 of cooling pad 20 (as adapted for use in connection with this type of support surface in the manner described below) are of particularly utility when the thermally controlled sheet of the present invention is used on a support which oscillates, the fasteners preventing, or at least reducing, any tendency of the cooling pad to move about on the top of the support surface 12.

Between side retention members 18a and 18b are pressure reduction inserts 13a, comprised of a foam material, for example, to support the arms of a patient when disposed in a supine position upon the therapeutic support platform apparatus 10. Likewise, between side retention members 18c and 18d are pressure reduction inserts 13b to support the legs of a patient. Also, between side retention members 18b of the therapeutic support platform are a rectal pressure reduction insert 11 and a top pressure reduction insert 13b. There also is a head pressure reduction insert 01 disposed between head retention members 16. While a number of inserts are shown for use with the therapeutic support platform 10 in order to accommodate different applications, it is understood that the number of inserts and material therefor may vary according to the desired need. For example, the pressure reduction surface insert could be a single piece configured to fit between the retention members 16, 18a, 18b, 18c, 18d and 17. Also, it is contemplated that the contours of the pressure reduction surface inserts can be varied as desired.

Figure 5:
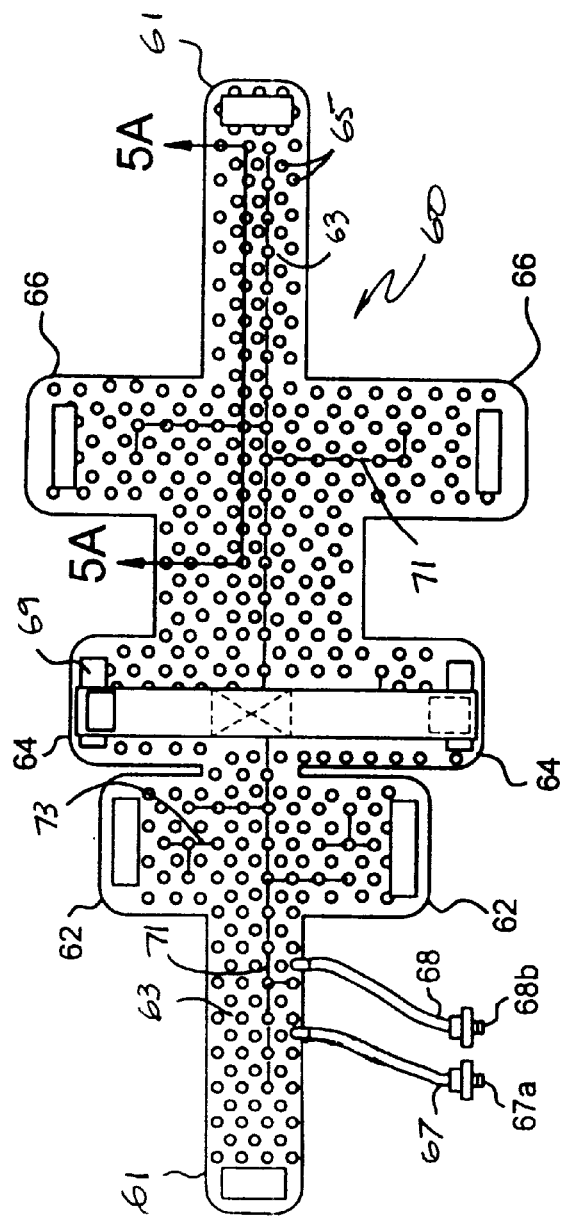
FIG. 5 is a plan view of a thermally controlled leg wrap, which is another embodiment of the present invention.
Figure 5A:
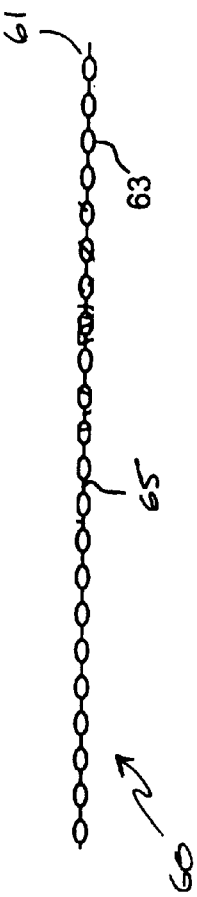
FIG. 5A is a cross-sectional view of the thermally controlled leg wrap as viewed in plan view in FIG. 5 taken along the lines 5—5 in FIG. 5.
Figure 6:
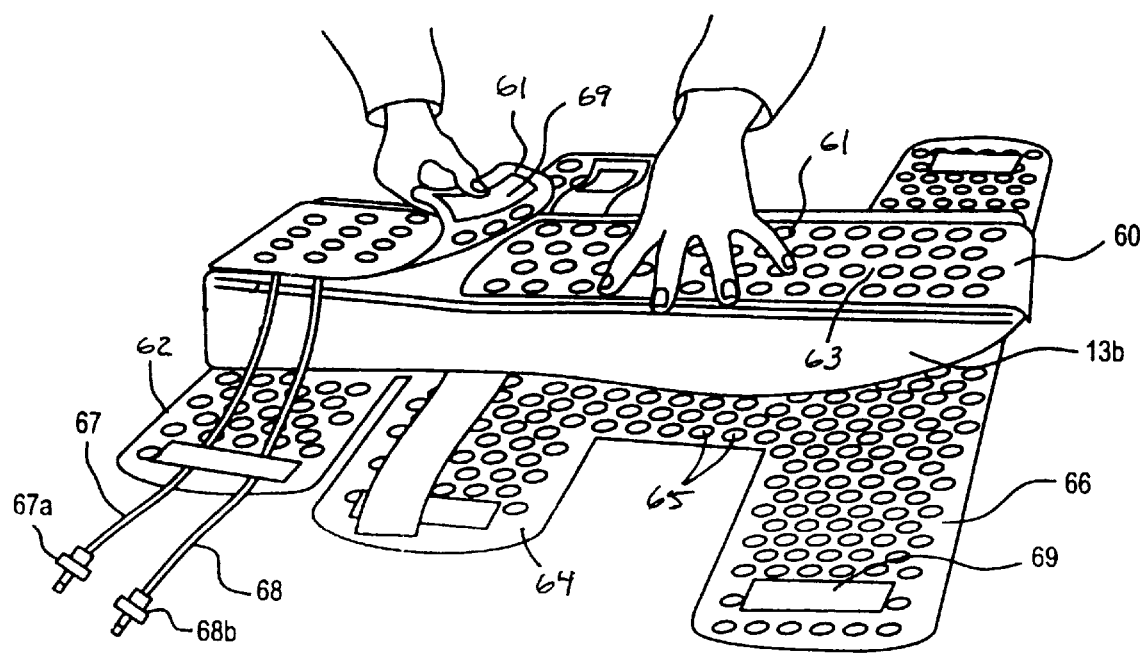
FIG. 6 illustrates a typical application of a thermally controlled leg wrap constructed in accordance with the teachings of the present invention utilizing a pressure reduction insert.

As shown in FIGS. 5, 5A, and 6, there is a thermally controllable leg wrap 60 made of a generally flexible, fluid impermeable material of the type described above in connection with the embodiments shown in FIGS. 1, 1A, and 2. The leg wraps 60 shown in FIGS. 5, 5A, and 6 are configured for use with the leg pressure reduction insert 13b. The leg wrap 60 has a first side 03 having a portion 09 positionable adjacent the patient support surface 12, a second side 05 having a first portion 04 thereof sealably connected to a first portion 06 of the first side 03 and a second portion 08 thereof spaced from a second portion 05 of the first side 03 such that there is formed a pocket 50 therebetween. Valves 67a and 68b with associated feed line 67 and return line 68 are operably connected to leg wrap 60 through their respective proximal ends and through their respective distal ends to a hyper-hypothermia fluid circulating device (not shown in FIGS. 5 and 6) as seen in FIG. 13 and described hereinafter to permit fluid flow therebetween.

Leg wrap 60 is provided with a flow directing weld 71 of the type and for the purpose described above in connection with the description of the thermally controlled sheet illustrated in FIGS. 1 and 1A. A plurality of flow directing auxiliary welds 73 are also provided for the purpose discussed above.

The leg wrap 60 has pairs of oppositely disposed arms 61, 62, 64 and 66, wherein each arm has a strip 69 of hook and pile fastener affixed thereto to permit fastening to itself or other cloth material. Arms 61 are used to envelop the leg pressure reduction insert 13b as shown in FIG. 6 and arms 62, 64 and 66 are shown lying over the side retention members 18c and 18d in FIG. 4 because, once the patient (not shown in FIG. 4) is supported on the therapeutic support 10, the arms 62, 64, and 66 are used to wrap about the patient's legs when disposed thereon. Referring to FIG. 5A, it can be seen that leg wrap 60 is provided with a plurality of fluid passages 63 for circulation of heat transfer fluid therethrough and holes, or cross passages, 65 for movement of air therethrough in the manner described above in connection with the embodiments shown in FIGS. 1, 1A, and 2.

Figure 8:
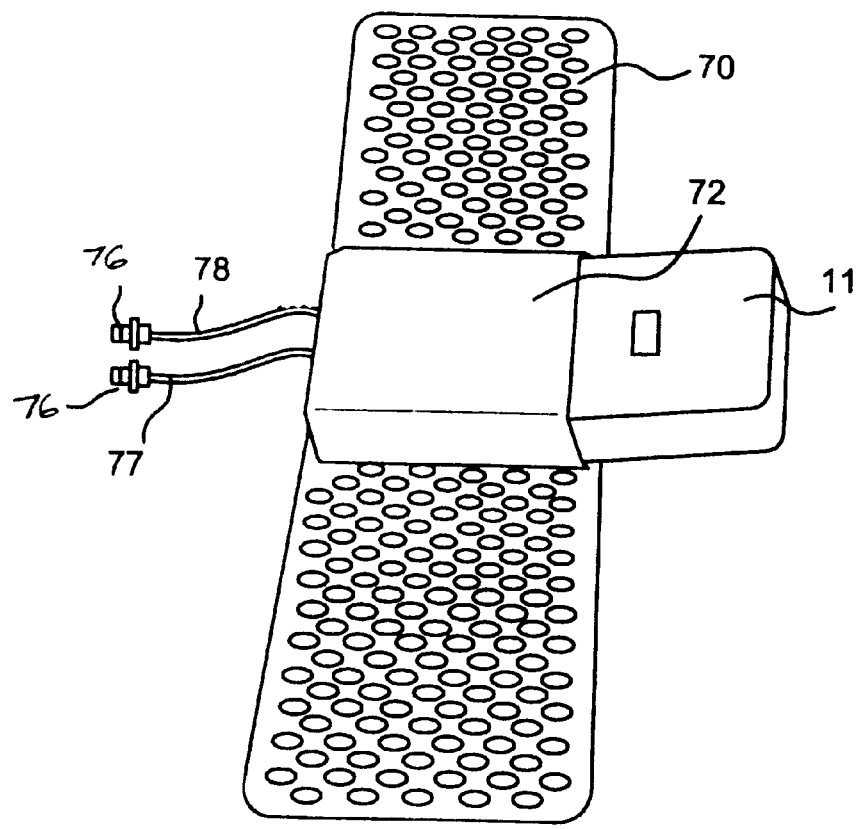
FIG. 8 illustrates a typical application of a thermally controlled mid-section wrap constructed in accordance with the teachings of the present invention utilizing a rectal pressure reduction insert.
Figure 7:
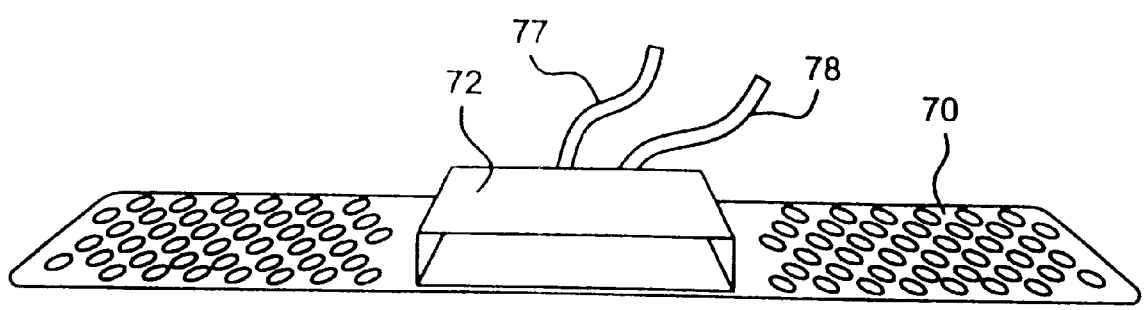
FIG. 7 illustrates a thermally controlled mid-section wrap, which is another embodiment of the present invention.

As shown in FIGS. 7 and 8, there is a thermally controllable midsection wrap 70 made of a generally flexible fluid impermeable material suitable for containing and directing the flow of fluids such as may be used for cooling patients. This material has been described in earlier embodiments. Midsection wrap 70 is configured for use as a rectal wrap having a retention sleeve 72 formed thereon to retain a rectal pressure reduction insert 11. Valves 76 with associated feed line 77 and return line 78 are also provided. As noted earlier, pad descriptions may be different and it should be understood that modifications do not depart from the scope of the invention.

Figure 9:
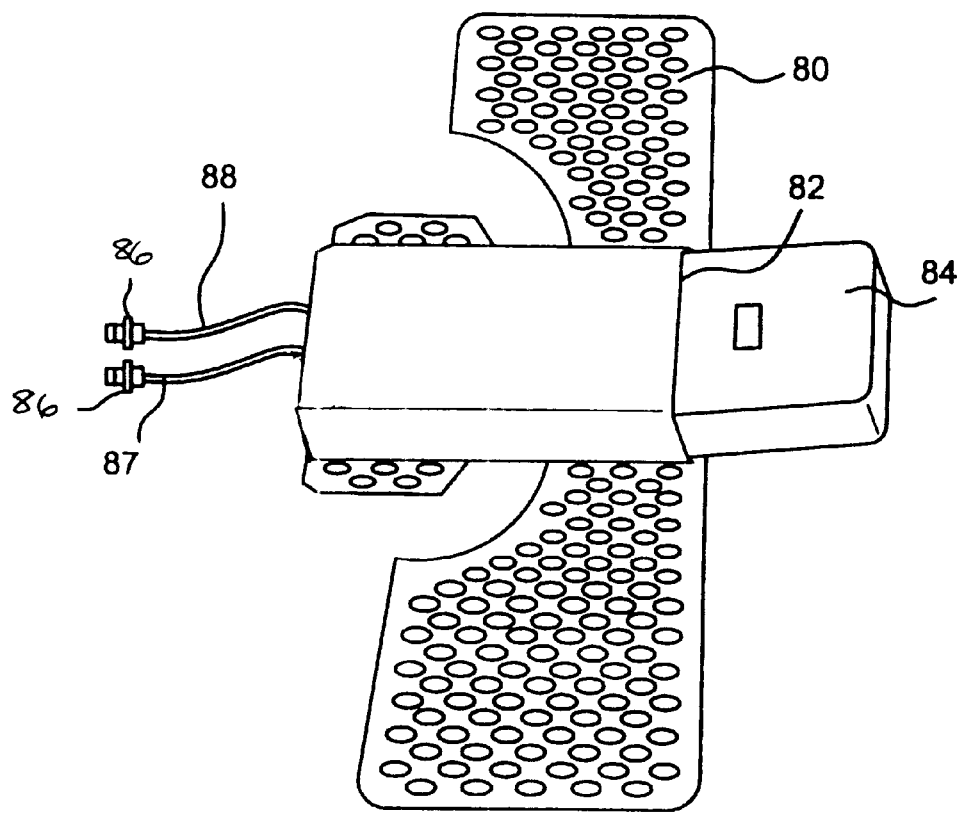
FIG. 9 illustrates a thermally controlled upper body wrap, which is another embodiment of the present invention, utilizing a thoracic cushion insert.

FIG. 9 shows a thermally controllable sheet constructed in accordance with the teachings of the present invention which is configured as an upper body wrap 80 having retention sleeve 82 formed thereon to retain the top pressure reduction insert 84. Valves 86 with associated feed line 87 and return line 88 are also provided. The upper body wrap is made of a generally flexible material to permit fluid flow there between as described in earlier embodiments. Again it should be noted that pad descriptions may be different and modifications do not depart from the scope of the invention.

Figure 10:
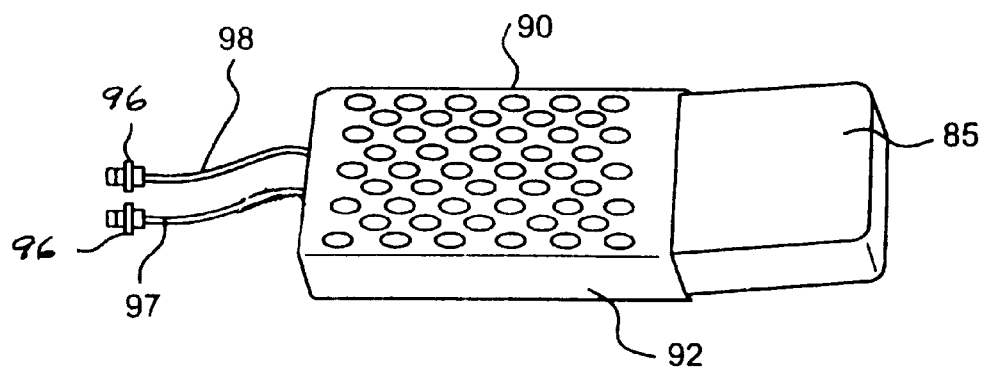
FIG. 10 illustrates a typical thermally controlled head wrap, which is another embodiment of the present invention, utilizing a cranial pressure reduction cushion.

As with the other embodiments, FIG. 10 shows another embodiment of the thermal control pad of the present invention in the form of a head wrap 90 having retention sleeve 92 formed thereon to retain the head pressure reduction insert 85. Valves 96 with associated feed line 97 and return line 98 are also included in this pad design. Again, as with earlier embodiments, this pad 90 is made with a generally flexible material as describe earlier and modifications to pad design do not detract from the scope of the invention.

Figure 11A:
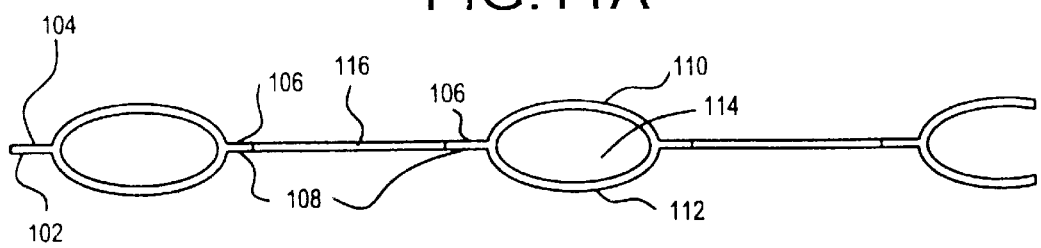
FIG. 11A is a cross-sectional view of the thermally controlled body wrap which is illustrated as FIG. 11 taken along the lines 11A—11A in FIG. 11.

FIGS. 11 and 11A show yet another alternate embodiment in which the thermally controlled sheet/pad of the present invention is configured as cooling pad 100 comprised of multiple layers of liquid passages which may be utilized in an alternating fashion to circulate heat transferred liquid first in one pattern and then a second pattern. The cooling pad 100 similarly has a first side 102 positionable adjacent the patient support surface 12, a second side 104 having a first portion 106 thereof sealably connected to a first portion 108 of the first side 102 and second portion 110 thereof spaced from a second portion 112 of the first side 102 such that there is formed a pocket 114 therebetween. Also, within the meeting surfaces 106 and 108 are open surfaces 116. Valves 118 with associated lines 120 are operably connected to the pocket 114 and connectable to hyper-hypothermia fluid producing device FIG. 13 to permit fluid flow therebetween. In an alternative embodiment (not shown), openings 116 may be replaced with alternate means for enabling evacuation of vapor of adjacent the patient's skin or to provide limited airflow in the same proximity.

Many variations in the design and configuration of the wraps 60, 70 and 80 and members 90 and 100 may be employed. For example, the material thereof as well as the fluids and fluid flow patterns formed there within can be altered as desired. In one alternative embodiment, separate fluid flow patterns are formed in a single wrap or member wherein the separate flow patterns are fed with different fluids or altered using a timed valve mechanism which switches the fluid paths after a predetermined period or as desired to provide changes in surface temperature and pressure.

Moreover, reference has been made herein to the use of a heat transfer fluid in contemplation of the use of a gas (or mix of gases) and/or liquids for controlling the temperature of the patient. For instance, in one embodiment, a thermally controlled sheet having a first flow pattern formed therein is air filled and the wrap or member may include restricted open surfaces along the flow pattern through which the air could continuously pass to further aid the patient. In a second embodiment in which the pad is provided with separate fluid flow patterns as described above, air is used in the first flow pattern and water is used as the heat transfer fluid in the second flow pattern and the flow of air and water is alternated and/or provided continuously at the same time. In still another modification of this second embodiment of a pad having separate fluid flow patterns and flows of both air and water heat transfer fluids, the pressure and/or flow rate at which either or both heat transfer fluid is provided to the respective separate fluid flow patterns is changed at intervals and/or continuously varied during the use of the pad to control the body temperature of the patient.

Referring now to FIG. 12 and to the schematic diagram set out in FIG. 13, there is shown a distribution system for the heat transfer fluid provided by hyper-hypothermia fluid flow device 58. Connected to the frame 14 (see FIG. 12) of the therapeutic support 12 are manifolds 122, 124 and 126 which are interconnected by feed lines 128 and return lines 130. The feed lines 56 and 67 to body wraps 60a and 60b, respectively, and return lines 57 and 68 are connected to a main manifold 122. Similarly, feed and return lines 77 and 78 for body wrap 70 are connected to manifold 122. Feed line 87 and return line 88 connect to top manifold 124 and feed line 97 and return line 98 connect to head manifolds 126.

Feed lines 132 and return lines 134 connect the hyper-hypothermia fluid producing device 58 to the main manifold 122. Lines 128 and 130 connect main manifold 122 to the top and head manifolds 124 and 126. The number of lines and manifolds are set forth by way of example and it is understood that their number may increase or decrease as desired.

FIG. 4 shows the wraps operatively disposed within the therapeutic support platform apparatus 10. Once the patient is disposed on the wraps 60, 70, 80 and 90, the patient is covered, if so desired, and fluid flow is initiated through the wraps 60, 70, 80 and 90 via the hyper-hypothermia fluid producing device 58 and manifolds 122, 124, and 126 as described above. Concurrently with the present invention, or as desired, the therapeutic support platform apparatus 10 can be operated to provide treatment, such as oscillatory or traction therapy.

By so providing, the present invention has resulted in an improved thermally controllable apparatus for use with a predetermined therapeutic support platform apparatus and a thermal fluid producing device. The thermally controllable apparatus enables the patient to be cooled or heated and/or aired while receiving treatment on a therapeutic support platform apparatus.

Figure 14:
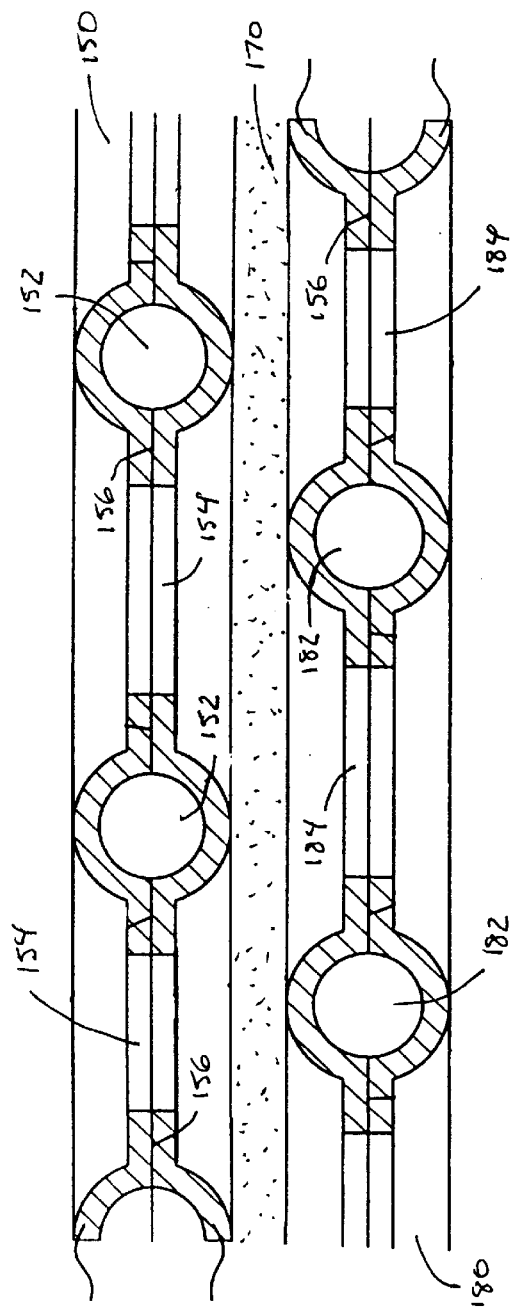
FIG. 14 is a sectional view through a portion of two thermally controlled sheets constructed in accordance with the teachings of the present invention which are overlaid, one upon the other, for alternately circulating a heat transfer fluid therethrough.

In another embodiment of the thermal control sheet of the present invention, multiple like wraps are overlaid one on top of the other with the fluid flow patterns slightly offset as shown in FIG. 14. In the embodiment shown in FIG. 14, a first thermally controlled sheet 150 overlays a second thermally controlled sheet 180. Each of the sheets 150 and 180 is constructed in the configuration shown, for instance, in FIGS. 1, 1A, and 2, and is provided with respective fluid passages 152 and 182 and cross passages 154 and 184 formed by the welds 156 and 186, respectively. Although not shown in FIG. 14 because of the scale of the drawing, each of the sheets 150 and 180 is supplied by separate fluid feed and return lines so that the sheets 150 and 180 are supplied with heat transfer fluids independently of each other, either directly from a hyper-hypothermia fluid flow device such as is shown at reference numeral 158 in FIG. 15 or from a manifold such as the manifold 160 shown in FIG. 15. Although not required to be used in this fashion, because the sheets 150 and 180 are supplied with heat transfer fluid separately, the sheets 150 and 180 may be operated at different pressures and/or fluid flow rates, or the pressure and/or fluid flow rates may be varied either continuously or periodically. Further, pressure and/or flow rates in the sheets 150 and 180 may be varied in or out of phase.

To provide for operation of the sheets 150 and 180 in this manner, manifold 160 is provided with solenoid-operated valves (labeled 2, 3, 4, and 5 on manifold 160 in FIG. 15) and the feed lines 162 and 167 supplying heat transfer fluid to sheets 150 and 180, respectively, are provided with pressure sensors, indicated schematically at reference numerals 163 and 165. The output from pressure sensors 163 and 165 is read by a microprocessor 166 programmed to continuously poll the sensors 163 and 165 and to open or close the solenoid-operated valves between manifold 160 and lines 162, 164, 167, and 168 as required to achieve an operator-selected set pressure (restricting the flow of return fluid from lines 164 and 168 increases pressure, varying the valves in the feed lines 162 and 167 with the valves in return lines 164 and 168 full open increases or decreases flow). The microprocessor is of a conventional type known in the art and is provided with know operator input set means and read-outs for interfacing with the operator.

Figure 15:
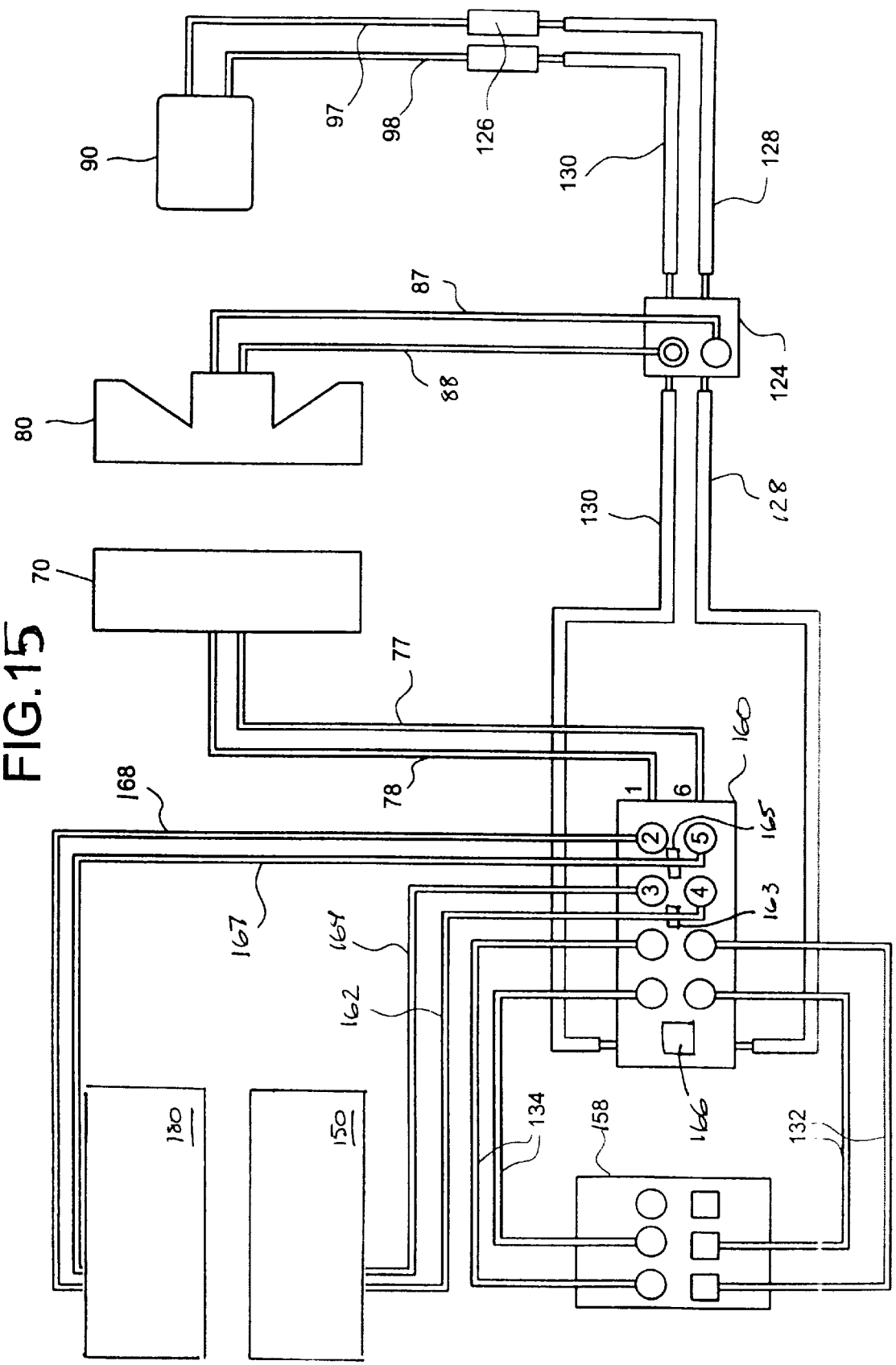
FIG. 15 is a schematic diagram of a control system for a plurality of thermally controlled pads for use with a patient support system.

In most other respects, the distribution of heat transfer fluid from hyper-hypothermia fluid flow device 158 is identical to that described in connection with FIG. 13 such that like reference numerals are used to designate the common parts thereof in FIG. 15. In addition to the differences resulting from the use of alternating sheets 150 and 180, however, FIG. 15 also shows solenoid-operated valves (labeled 1 and 6) between manifold 160 and lines 77 and 78 in fluid communication with midsection wrap 70 to provide additional control over patient body temperature and/or provide varying pressures to the portion of the patient's body which may be resting on a portion of the midsection wrap 70.

Referring once again to FIG. 14, the first and second sheets 150 and 180 are overlaid so that the fluid passages 152 and 182 are "staggered" when viewed in the cross-sectional view shown in the figure. In other words, the holes comprising cross passages 154 and 184 are situated over the dimples comprising fluid passages 152 and 182. This staggered, or alternating, arrangement of the sheets 150 and 180 provides for increased air flow, for instance from a low air loss patient support surface, through cross passages 154 and 184. To maintain the flow of air through cross passages 154 and 184, it will be noted that the dimples/fluid passages 152 and 182 of first sheet 150 are not aligned directly over the holes/cross passages 154 and 184 of second sheet 180. Arranging the sheets 150 and 180 in this relationship prevents the dimples and holes created by the fluid passages 152, 182 from slipping into the respective holes of cross passages 154, 184 of the opposing sheet 150, 180, thereby preventing the holes from becoming partially closed or even blocked by the opposing dimple.

In a particularly preferred embodiment as shown in FIG. 14, a layer of air permeable fabric 170 is interposed between sheets 150 and 180. Fabric 170 may be comprised of any suitable fabric for passing air or even a loosely woven or non-woven fabric with pores which allow free passage of air therethrough. Fabric layer 170 serves multiple functions depending upon its composition. For instance, if a high loft, loosely woven fabric is utilized, the primary function may be maintaining the flow of air through the cross passages 154, 184 of sheets 150, 180. Such fabric layers may be so effective at maintaining air flow through the passages 154, 184 that alignment of the holes and dimples of sheets 150, 180 need not be maintained in the manner described above, satisfactory air flow being maintained even if the dimples of sheets 150, 180 are interdigitated with the opposing holes. Another type of fabric layer 170 which is utilized to advantage is comprised of a fabric which is highly water absorbent such as the material comprising the DRIFLO™ pad described above. Such a fabric layer serves as both an incontinence pad and to absorb any condensation, perspiration, or other moisture which may be present in the interface between the patient's skin and the therapeutic support surface 12, thereby providing optimal conditions for proper patient skin care.

The above described embodiments are set forth by way of example and are not for the purpose of limiting the present invention. It will be readily apparent to those skilled in the art that obvious modifications and variations can be made to the embodiments while still capturing novel aspects of the invention and without departing from the scope of the invention. Accordingly, the claims appended hereto should be read in their full scope including any such modifications and variations as well as equivalents to the elements claimed. When reading these claims, do not be constrained by any particular word or phrase, but consider them as far-reaching as the law will permit in light of any particular prior art reference that may be in the same particular field of art.

What is claimed is:

1. A device for cooling a patient by means of a flow of chilled heat transfer liquid, comprising: a cooling pad having a length, a width, and a thickness comprising a plurality of primary and secondary heat transfer liquid passages, wherein each primary passage intersects at least three secondary passages; an array of holes between said passages, said holes extending throughout the entire thickness of the pad; and an inlet and an outlet for facilitating the flow of chilled heat transfer liquid.

2. A pad according to claim 1 wherein said pad is additionally adapted for placement directly under said patient and intermediate a patient support surface.

3. A pad according to claim 2 wherein said pad is fabricated with a relatively flat construction so that a first face of said pad faces said patient support surface and a second face of said pad faces away from said patient support surface.

4. A pad according to claim 3 wherein when in use, said first face is opposite said second face thereby allowing said flow of said chilled heat transfer liquid beneath said patient to cool said patient.

5. A pad according to claim 2 wherein said array of holes facilitates passages of waste fluids through said hole array in a direction generally perpendicular to the direction of flow of said heat transfer liquid through said passages.

6. A pad according to claim 5 wherein when in use the direction of passage of waste fluids through said hole array is away from said patient towards said patient support surface.

7. A thermally controllable device for use with a patient upon a patient support surface comprising: a cooling pad with peripheral edges, an interior, and a thickness; thermal liquid supply apparatus that supplies thermal transfer liquid to said cooling pad; wherein said cooling pad comprises a thermally conductive top sheet and a thermally conductive bottom sheet, wherein the top sheet and bottom sheet are connected along the peripheral edges and at a plurality of isolated connection points within the interior, each connection point being entirely surrounded by thermal liquid passages for the flow of a thermal heat transfer liquid within the pad; and the plurality of spaced connection points comprises an array of holes that extend throughout the entire thickness of said cooling pad, said array of holes allowing waste fluids to pass through the pad; and a fluid port operably connected between the thermal liquid passages and said thermal liquid supply apparatus to permit flow of said thermal transfer liquid therebetween.

8. A device according to claim 7 wherein said array of holes allows passage of said waste fluids through the pad in a direction generally perpendicular to the direction of flow of said thermal transfer liquid within the pad.

9. A device according to claim 8 wherein said pad is adapted to be placed intermediate said patient and said patient support surface.

10. A device according to claim 9 wherein when in use, said passage of waste fluids through said holes is from said patient towards said patient support surface.

* * * * *